(12) United States Patent
Lin et al.

(10) Patent No.: US 11,656,222 B2
(45) Date of Patent: May 23, 2023

(54) SENSOR USING ULTRASOUND TO DETECT TARGET SUBSTANCE AND DETECTING DEVICE USING SAME

(71) Applicant: HON HAI PRECISION INDUSTRY CO., LTD., New Taipei (TW)

(72) Inventors: Hsin-Hua Lin, New Taipei (TW); Wei-Chih Chang, New Taipei (TW); Po-Li Shih, New Taipei (TW); Chao-Chun Yang, New Taipei (TW); I-Min Lu, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 541 days.

(21) Appl. No.: 16/833,904

(22) Filed: Mar. 30, 2020

(65) Prior Publication Data
US 2021/0109092 A1   Apr. 15, 2021

(30) Foreign Application Priority Data
Oct. 10, 2019   (CN) .......................... 201910957992.X

(51) Int. Cl.
*G01N 33/53*   (2006.01)
*G01N 29/22*   (2006.01)
*G01N 29/036*   (2006.01)

(52) U.S. Cl.
CPC ....... *G01N 33/5308* (2013.01); *G01N 29/036* (2013.01); *G01N 29/22* (2013.01)

(58) Field of Classification Search
CPC .. G01N 33/5308; G01N 29/036; G01N 29/22; G01N 29/02; G01N 29/022; G01N 29/222
(Continued)

(56) References Cited
U.S. PATENT DOCUMENTS 6,854,338 B2 * 2/2005 Khuri-Yakub .......... G01F 1/667
73/861.27
8,424,370 B2 * 4/2013 Cable ................. G01N 29/2406
73/64.53
(Continued)

FOREIGN PATENT DOCUMENTS

CA       2624664 A1 * 4/2007  .......... G01N 27/221
CN   102520147 A  *  6/2012
(Continued)

*Primary Examiner* — Lisa M Caputo
*Assistant Examiner* — Rose M Miller
(74) *Attorney, Agent, or Firm* — ScienBiziP, P.C.

(57) ABSTRACT

A sensor using ultrasound to detect presence and nature of analyte includes an ultrasonic element and a receptor thereon. The ultrasonic element includes a first electrode, a second electrode facing and spaced apart from the first electrode, an insulating layer between the first electrode and the second electrode, and a vibrating film between the insulating layer and the first electrode. The vibrating film carries the first electrode. A cavity is formed between the vibrating film and the insulating layer. The receptor is on a side of the first electrode away from the second electrode. The receptor can combine with a target substance in a test analyte. When the first electrode and the second electrode are applied with different voltages, certain ultrasound frequencies are generated as the vibrating film vibrates, and the presence and weight of different target substances are indicated by the changes in resonance.

8 Claims, 7 Drawing Sheets

(58) Field of Classification Search
USPC ............... 73/579, 54.41, 61.71, 61.79, 64.53
See application file for complete search history.

(56) References Cited

U.S. PATENT DOCUMENTS

| | | | |
|---|---|---|---|
| 9,857,243 B2 * | 1/2018 | Wilkinson | ........... G01N 29/022 |
| 10,036,730 B2 * | 7/2018 | Wilkinson | ......... G01N 29/2437 |
| 11,253,856 B2 | 2/2022 | Kosaka et al. | |
| 2002/0083771 A1 * | 7/2002 | Khuri-Yakub | ....... G01N 29/223 |
| | | | 73/64.53 |
| 2014/0364325 A1 * | 12/2014 | Cable | ................. G01N 29/2406 |
| | | | 506/17 |
| 2015/0143911 A1 * | 5/2015 | Takahashi | .......... G01N 21/1702 |
| | | | 73/643 |

FOREIGN PATENT DOCUMENTS

| | | | | |
|---|---|---|---|---|
| CN | 104655261 A | 5/2015 | | |
| CN | 107918206 A | 4/2018 | | |
| CN | 110057907 A | 7/2019 | | |
| WO | 20180200872 A1 | 11/2018 | | |
| WO | WO-2021028827 A1 * | 2/2021 | ............. | G01H 11/00 |

* cited by examiner

SENSOR USING ULTRASOUND TO DETECT TARGET SUBSTANCE AND DETECTING DEVICE USING SAME

FIELD

The subject matter herein generally relates to sensors and a detecting device using the sensor.

BACKGROUND

A receptor or an adsorbent is usually combined with a target substance in a test analyte to determine whether the test analyte contains the target substance. However, this detection method not only needs to create conditions for combination of the receptor and the target substance, but also needs to detect whether the receptor or adsorbent has combined with the target analyte. There are many methods to detect whether the receptor or adsorbent has combined with the target analyte. For example, a by-product may be generated and be detected when a biochemical reaction occurs between the receptor and the target analyte. Alternatively, a pH value may be determined when the receptor binds the target analyte, or a weight of the test analyte may be detected if the weight of test analyte does change when the receptor is combined with the target analyte.

SUMMARY

The present disclosure provides a sensor including an ultrasonic element. The ultrasonic element includes a first electrode, a second electrode facing and spaced apart from the first electrode, an insulating layer on a side of the second electrode adjacent to the first electrode, a vibrating film between the insulating layer and the first electrode, and a receptor on a side of the first electrode away from the second electrode. The vibrating film carries the first electrode. A cavity is formed between the vibrating film and the insulating layer. The receptor is configured to be combined with a target substance in a test analyte. The vibrating film is configured to vibrate to produce ultrasonic waves when the first electrode and the second electrode are applied with different voltages.

The present disclosure also provides a detection device including a hollow pipe defining two openings and at least one sensor in the hollow pipe. Each sensor includes an ultrasonic element. The ultrasonic element includes a first electrode, a second electrode facing and spaced apart from the first electrode, an insulating layer on a side of the second electrode adjacent to the first electrode, a vibrating film between the insulating layer and the first electrode, and a receptor on a side of the first electrode away from the second electrode. The vibrating film carries the first electrode. A cavity is formed between the vibrating film and the insulating layer. The receptor is configured to be combined with a target substance in a test analyte. The vibrating film is configured to vibrate to produce ultrasonic waves when the first electrode and the second electrode are applied with different voltages.

The present disclosure also provides a detection device. The detection device includes a first electrode, a second electrode facing and spaced apart from the first electrode, a channel between the first layer and the second layer, and at least one sensor in the channel. Each sensor includes an ultrasonic element. The ultrasonic element includes a first electrode, a second electrode facing and spaced apart from the first electrode, an insulating layer on a side of the second electrode adjacent to the first electrode, a vibrating film between the insulating layer and the first electrode, and a receptor on a side of the first electrode away from the second electrode. The vibrating film carries the first electrode. A cavity is formed between the vibrating film and the insulating layer. The receptor is configured to be combined with a target substance in a test analyte. The vibrating film is configured to vibrate to produce ultrasonic waves when the first electrode and the second electrode are applied with different voltages.

BRIEF DESCRIPTION OF THE DRAWINGS

Implementations of the present technology will now be described, by way of embodiments only, with reference to the attached figures.

DETAILED DESCRIPTION

Figure 1:
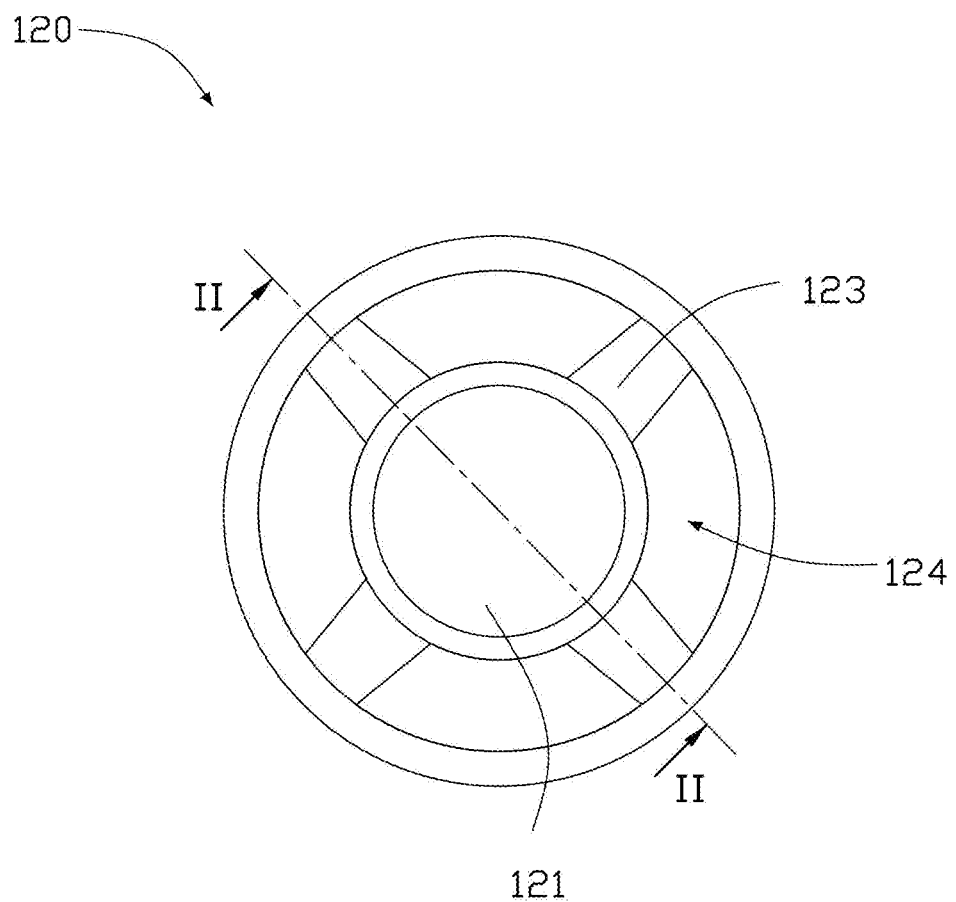
FIG. 1 is a plan view of an ultrasonic element of the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Figure 2:
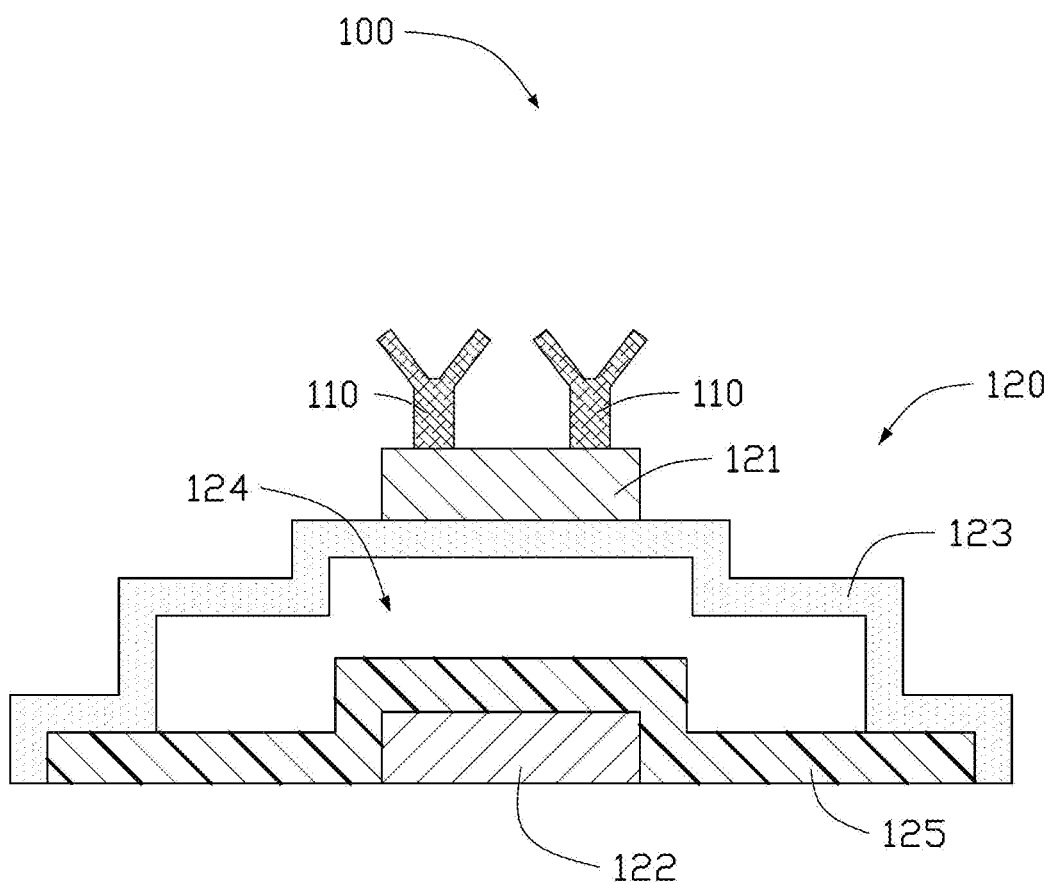
FIG. 2 is a cross-sectional view of a sensor.

FIG. 1 shows an ultrasonic element 120. FIG. 2 shows a sensor 100 including the ultrasonic element 120 and a receptor 110 on the ultrasonic element 120. The ultrasonic element 120 may be a capacitive micromachined ultrasonic transducer (CMUT), which includes a first electrode 121, a second electrode 122 facing and spaced apart from the first electrode 121, an insulating layer 125 between the first electrode 121 and the second electrode 122, and a vibrating film 123 between the insulating layer 125 and the first electrode 121. The first electrode 121 and the second electrode 122 are electrically insulated from each other. The insulating layer 125 covers the second electrode 122. The first electrode 121 is formed on the vibrating film 123 and the vibrating film 123 carries the first electrode 121. A cavity 124 is formed between the insulating layer 125 and the vibrating film 123. The cavity 124 provides a space for the vibrating of the vibrating film 123.

When the sensor 100 operates, the first electrode 121 and the second electrode 122 are fed direct voltages, and an electrostatic field is formed between the first electrode 121 and the second electrode 122. The electrostatic field will pull a portion of the vibrating film 123 on a side of the first electrode 121 toward the second electrode 122. Then the first electrode 121 and the second electrode 122 are applied with alternating voltages, and electric fields are generated and change under the alternating voltages, which causes the vibrating film 123 to vibrate up and down. The ultrasonic element 120 generates ultrasonic waves in a predetermined frequency range by physically vibrating of the vibrating film 123. The receptor 110 is on a side of the first electrode 121 away from the vibrating film 123.

Figure 3:
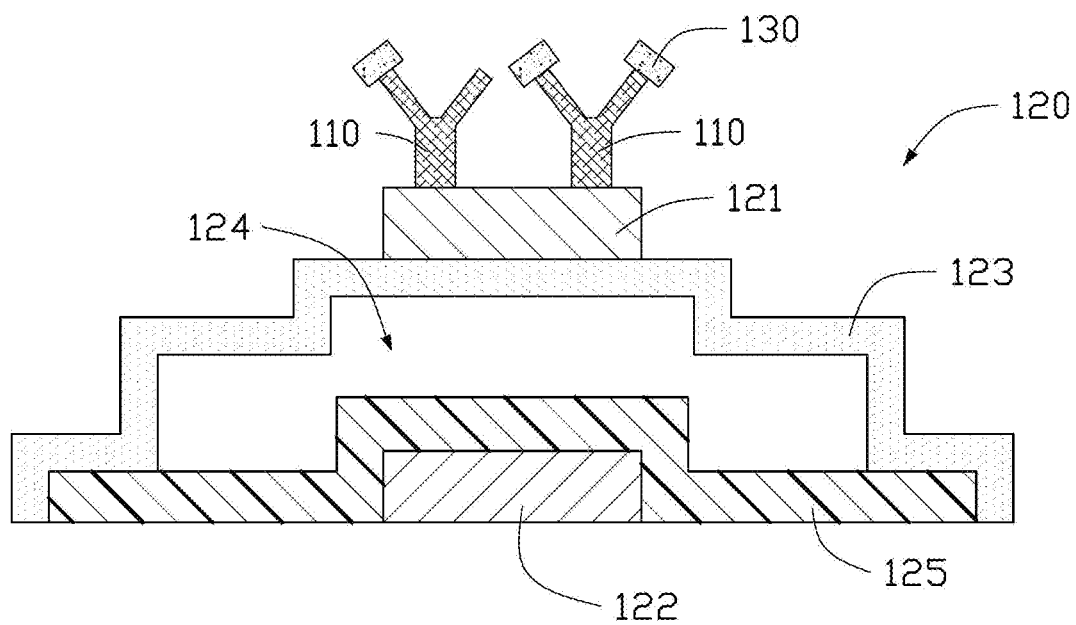
FIG. 3 is a cross-sectional view showing a combination of the sensor of FIG. 2 and a target substance to be measured.

The receptor 110 is configured for combining with a target substance 130 in a test analyte. The test analyte may be a liquid, a gas, or a solid. As shown in FIG. 3, when the target substance 130 is included in the test analyte, a combination of the target substance 130 and the receptor 110 on the first electrode 121 will cause change in weight carried by the vibrating film 123, which affects a vibration amplitude of the vibrating film 123. The frequency range of the ultrasonic wave of the ultrasonic element 120 is affected, such that the frequency range of the ultrasonic wave changes.

Figure 4:
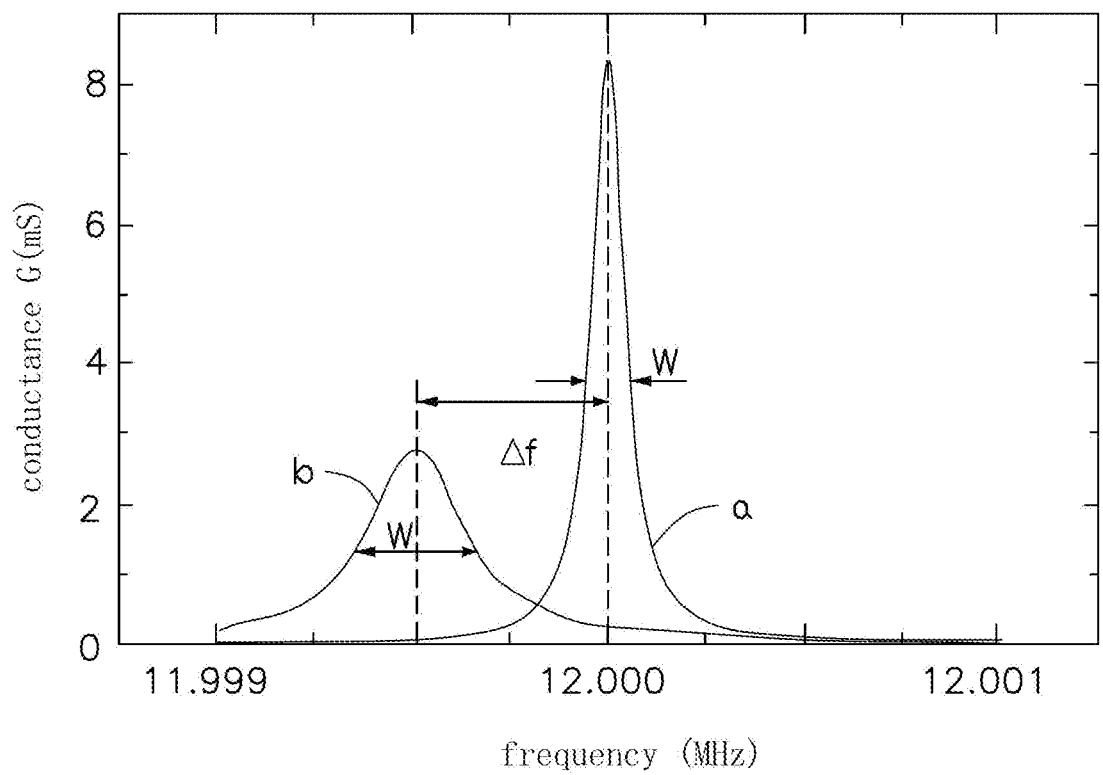
FIG. 4 is a frequency-conductance curve diagram before and after the sensor is combined with a target substance.

FIG. 4 shows frequency-conductance curves of the ultrasonic element 120 measured by an impedance analyzer, wherein the curve a represents a frequency-conductance curve of the ultrasonic element 120 before the receptor 110 is combined with the target substance 130. The curve b represents a frequency-conductance curve of the ultrasonic element 120 after the receptor 110 is combined with the target substance 130. The difference between the curve a and the curve b shows that the frequency ranges of the ultrasonic wave emitted by the ultrasonic element 120 are significantly different.

It can be seen from the curve a that the conductance has a maximum value at a frequency of 12 MHz when the receptor 110 is not combined with the target substance 130 in the test analyte. It can be seen from the curve b that the conductance has a maximum value when the frequency of the ultrasonic wave is between 11.999 MHz and 12 MHz (about 11.9995 MHz) when the receptor 110 is combined with the target substance 130 in the test analyte.

In this embodiment, a frequency corresponding to the maximum conductance of the ultrasonic element 120 when the receptor 110 is combined with the target substance 130 is less than a frequency corresponding to the maximum conductance of the ultrasonic element 120 when the receptor 110 is not combined with the target substance 130. Therefore, when the relationship between the frequency and the conductance of the ultrasonic element 120 changes to a certain extent, it can be inferred that the receptor 110 has been combined with the target substance 130, and then it can be determined that the test analyte contains the target substance 130. Such changes can be detected by an ultrasonic frequency detection device (for example, an impedance analyzer).

The receptor 110 may be a chemical adsorbent, such as an organic polymer, a porous material, nanoparticles, a metal film, or the like. The receptor 110 may be a biological receptor, for example an antibody, a catalyst, protein, DNA, ribonucleic acid (RNA), complementary DNA (CDNA), and derivatives thereof. The sensor 100 provided in this embodiment can function as a biosensor or a chemical sensor.

When the receptor 110 is a solid and is mixed with a liquid, the receptor 110 can be spray-printed on the side of the first electrode 121 away from the vibrating film 123 by Ink-Jet Printing (IJP). The receptor 110 can be selected according to the type of the target substance 130. Examples of the receptor 110 and the target substance 130 are listed in Table 1.

TABLE 1

| Target Substance | Receptor |
|---|---|
| Sulfide | Poly (4-vinylphenol), poly (N-vinylpyrrolidone), poly (styrene) |
| ketone | Polyaniline, polypyrrole, poly (N-methylmethacrylate), poly (9-vinylcarbazole) |
| alcohol | Poly (N-vinylpyrrolidone), poly (methylmethacrylate), polyaniline |
| Alkenes | Poly (4-vinylphenol), poly (vinyl acetate), poly (styrene) |
| prostate specific antigen (PSA) | Monoclonal antibodies |
| DNA | Restriction enzyme |

When the target substance 130 is a sulfide, a ketone, an alcohol, or an olefin, the receptor 110 may include a polymerizable polymer. When the target substance 130 is an antigen, the receptor 110 may include a corresponding antibody. When the target substance 130 is DNA, the receptor 110 may include a restriction enzyme. According to different target substances 130 and different receptors 110, the sensor 100 can be applied for different purposes, such as human volatile organic compound (VOC) detection, environmental VOC detection, pesticide detection, and food safety detection. When a detection device having the sensor 100 is used to detect a test analyte, the detection process is simple.

Figure 5:
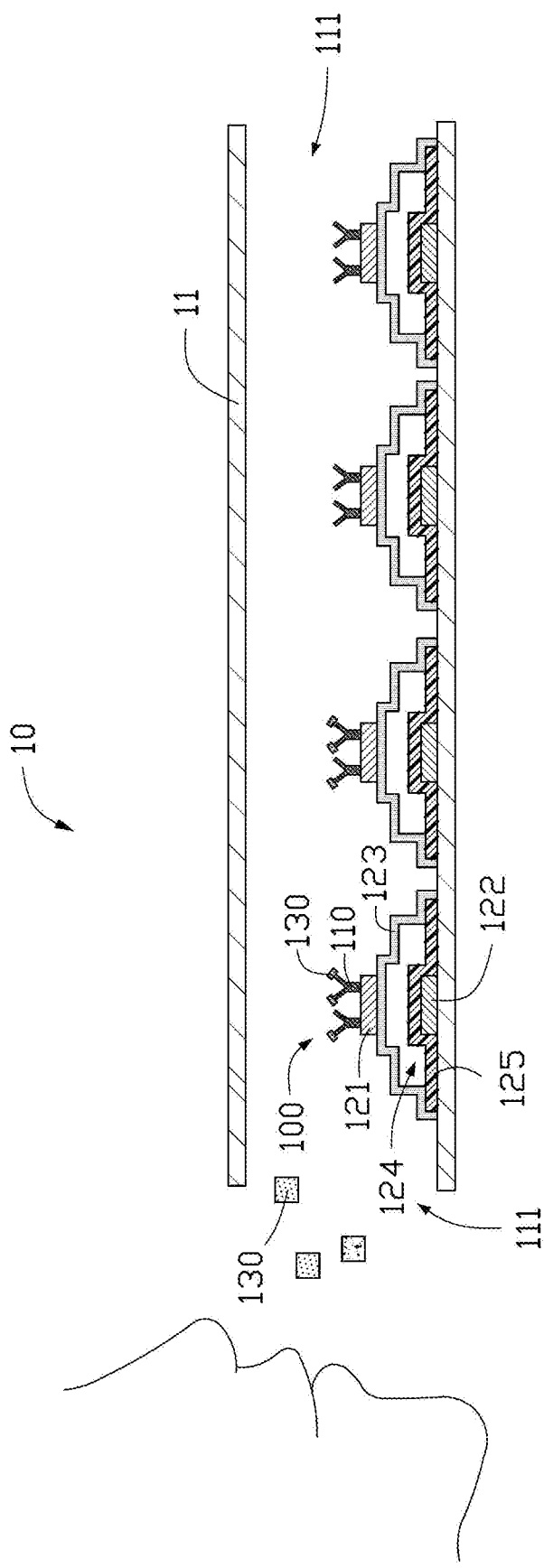
FIG. 5 is a cross-sectional view of a gas detection device.

FIG. 5 shows a detection device 10. The detection device 10 can be configured to detect whether a target substance 130 is contained in a gas analyte. The detection device 10 includes at least one sensor 100 and a hollow pipe 11. The hollow pipe 11 has opposite ends and defines one opening 111 at each end. The hollow pipe may be made of a corrosion-resistant material, such as glass. The at least one sensor 100 is on an inner wall of the hollow pipe 11.

The gas analyte enters into the hollow pipe 11 by one opening 111 of the hollow pipe 11 and flows across the plurality of sensors 100 on the inner wall of the hollow pipe 11. If the gas analyte does contain the target substance 130, the target substance 130 will combine with the receptor 110 of the sensor 100, resulting in a change in the frequency of the ultrasonic element 120. In other words, if the frequency of the ultrasonic wave changes, it means that the gas analyte does contain the target substance 130. By detecting the magnitude of change in the ultrasonic frequency, the content of the target substance 130 in the gas analyte can be estimated. The detection device 10 of this embodiment can be applied to detection of VOC of human exhalations. For example, to detect whether the exhaled gas contains the target substance 130, simply exhaling into one opening 111 of the hollow pipe 11 toward interior of the hollow pipe 11 allows result to be quickly obtained according to the change of the sensor 100. The detection process is time-saving and efficient.

Figure 6:
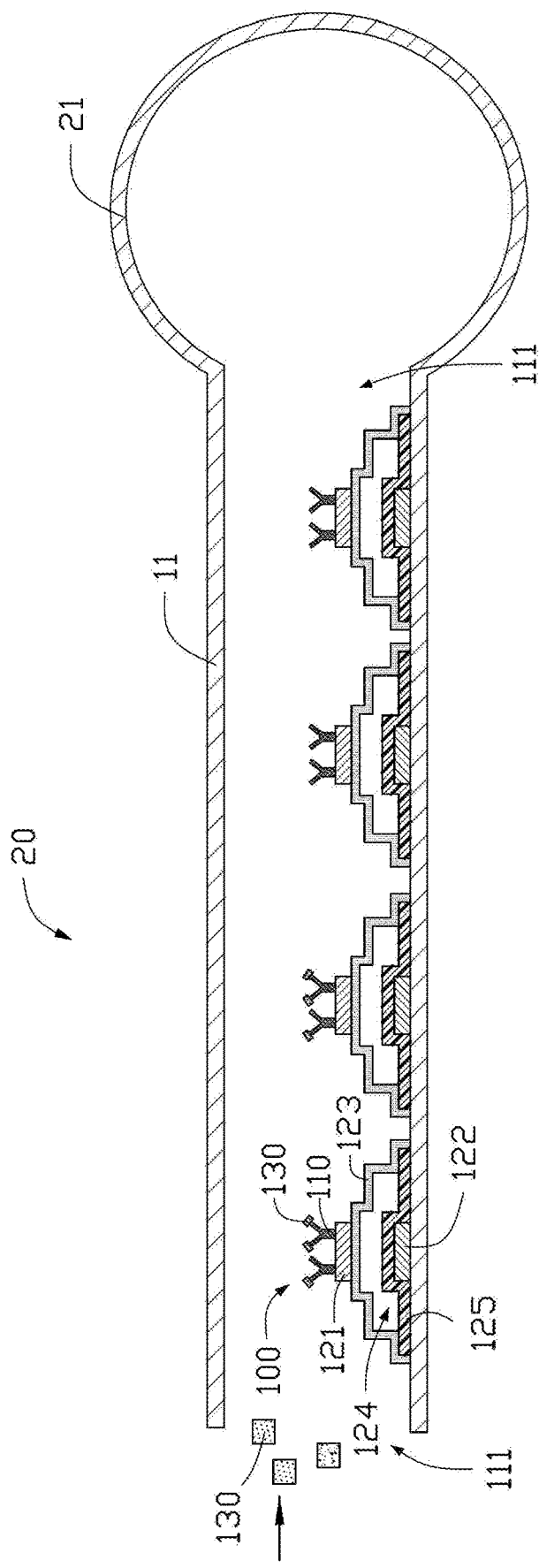
FIG. 6 is a cross-sectional view of a liquid detection device.

FIG. 6 shows a detection device 20. The detection device 20 can be configured to detect whether a target substance 130 is contained in a liquid analyte. The detection device 10 includes at least one sensor 100 and a hollow pipe 11. The detection device 20 includes a hollow pipe 11 and at least one sensor 100 in the hollow pipe 11 as the same in the detection device 10, and also includes a suction ball 21 coupled to the hollow pipe 11 which seals one opening 111 of the hollow pipe 11. The suction ball 21 may be made of a squeezable rubber material.

By squeezing the suction ball 21, the liquid analyte is sucked from one end of the hollow pipe 11 away from the suction ball 21 into the hollow pipe 11 and flows through the hollow pipe 11. If the liquid analyte contains the target substance 130, the target substance 130 will combine with the receptor 110 of the sensor 100. Then it can be determined whether the target substance 130 is contained in the liquid analyte by detecting whether the frequency of the ultrasonic wave changes, and finally the liquid analyte will flow into the suction ball 21. In this embodiment, the suction ball 21 is made of rubber. In other embodiments, the suction ball 21 may be made of other elastic materials. The detection device 20 of this embodiment can be applied to, for example, the detection of VOCs in drinking water or surface water. The detection process is convenient. First the suction ball 21 is squeezed when one end of the hollow pipe 11 away from the suction ball 21 is in contact with water or other liquid, and the squeeze is released. It can be known whether the liquid analyte contains the target substance 130 according to a change of the sensor 100. The detection process is simple and convenient, and the detection is accurate and efficient.

Figure 7:
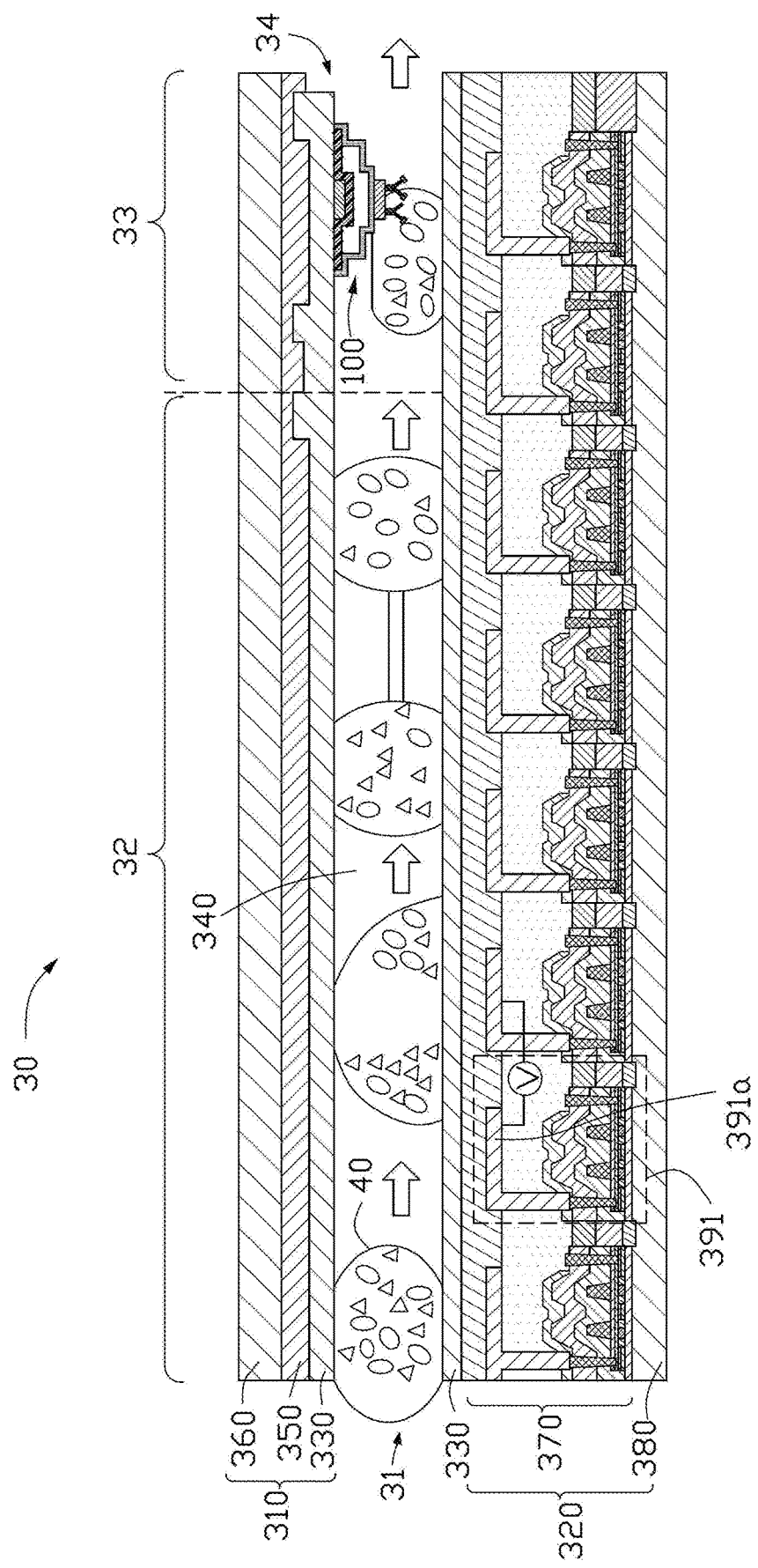
FIG. 7 is a cross-sectional view of a deoxyribonucleic acid (DNA) detection device.

FIG. 7 shows a DNA detection device 30. The DNA detection device 30 includes a first layer 310, a second layer 320 facing and spaced apart from the first layer 310, and a channel 340 formed between the first layer 310 and the second layer 320. The channel 340 allows the cell fluid analyte to flow through. The DNA detection device 30 is divided into a filtering section 32 and a detection section 33 coupled to the filtering section 32. A portion of the first layer 310 is in the filtering section 32, other portion of the first layer 310 is in the detection section 33. A portion of the second layer 320 is in the filtering section 32, other portion of the second layer 320 is in the detection section 33. The filtering section 32 defines a liquid inlet 31 at an end of the filtering section 32 away from the detection section 33. The detection section 33 defines a liquid outlet 34 at an end of the detection section 33 away from the filtering section 32. The DNA detection device 30 further includes at least one sensor 100 in the detection section 33.

The liquid inlet 31 allows the cell fluid analyte to flow into the filtering section 32, and the liquid outlet 34 allows the cell fluid analyte to flow out of the DNA detection device 30 after going through the detection section 33. The first layer 310 includes a hydrophobic layer 330, an electrode layer 350, and a first capping layer 360 stacked in that order. The electrode layer 350 is between the hydrophobic layer 330 and the first capping layer 360. The hydrophobic layer 330 of the first layer 310 is adjacent to the channel 340. The second layer 320 includes a hydrophobic layer 330, a thin film transistor array layer 370, and a second capping layer 380 stacked in this order. The thin film transistor array layer 370 is between the hydrophobic layer 330 and the second capping layer 380. The hydrophobic layer 330 is adjacent to the channel 340. The channel 340 couples both the liquid inlet 31 and the liquid outlet 34.

The sensor 100 is positioned on an inner wall of the channel 340 of the detection section 33. In this embodiment, the sensor 100 is positioned on a surface of the hydrophobic layer 330 of the first layer 310. The cell fluid analyte flows into the filtering section 32 from the liquid inlet 31, then flows into the detection section 33, and is examined in the detection section 33. Both the first capping layer 360 and the second capping layer 380 are electrically insulative to protect the DNA detection device 30.

As shown in FIG. 7, the hydrophobic layer 330 of the first layer 310 and the hydrophobic layer 330 of the second layer 320 form the inner wall of the channel 340. The thin film transistor array layer 370 includes a plurality of thin film transistors 391 arranged in an array. Each thin film transistor 391 is a conventional low-temperature polysilicon (LTPS) thin film transistor and includes a source electrode 391a. An electric field inside the channel 340 is formed by applying different voltages to the electrode layer 350 and the source electrode 391a of the thin film transistor 391, and a wetting performance of the cell fluid on the hydrophobic layer 330 can be adjusted by adjusting voltages applied to the electrode layer 350 and the thin film transistor array layer 370, thereby controlling a flow velocity of the cell fluid in the channel 340.

When using the DNA detection device 30 of this embodiment to perform DNA detection, the cell fluid analyte is first treated by a centrifuge, and the cell fluid analyte is introduced into the DNA detection device 30 from the liquid inlet 31. The purpose of the cell fluid flowing through the filtering section 32 by the channel 340 is to obtain a predicted DNA fragment for detection. Therefore, in order to completely separate the DNA from the cell in the filtering section 32 after the cell fluid analyte is introduced into the channel 340, a film-dissolving agent may be added to the channel 340, so that the cell membrane is dissolved to release internal substance (such as DNA) of the cell. The DNA being negatively charged, the DNA in the cell fluid analyte can be adsorbed on the hydrophobic layer 330 of the second layer 320 under the electrostatic field. At the same time, a restriction enzyme solution is added into the channel 340 of the filtering section 32. When a predicted DNA fragment is contained in the DNA, the restriction enzyme can extract the desired predicted DNA fragment (the target substance). If the DNA does not contain the predicted DNA fragment, the restriction enzyme cannot extract it. After that, the voltage between the electrode layer 350 and the thin film transistor array layer 370 is adjusted so that the cell fluid containing the restriction enzyme (which may or may not contain the predicted DNA fragment) flows forward and enters into the detection section 33.

The cell fluid containing the restriction enzyme solution flows through the detection section 33 after passing through the filtering section 32, and the detection section 33 detects whether the cell fluid includes the predicted DNA fragment. The detection section 33 is provided with the sensor 100 described above, and the first electrode 121 of the sensor 100 is provided with the receptor 110 for binding to the predicted DNA fragment. The frequency range, or changed frequency range, of the ultrasonic wave emitted by the sensor 100 determines whether the receptor 110 combines with the predicted DNA fragment, and then determines whether the cell contains the predicted DNA fragment. When a predicted fixed DNA fragment is contained in the DNA and the predicted DNA fragment in the cell fluid containing the restriction enzyme solution flows through the detection section 33, the predicted DNA fragment combines with the receptor 110. The frequency range of the ultrasonic wave emitted by the sensor 100 changes, thereby determining that the cell contains the predicted DNA fragment, otherwise it is determined that the cell does not contain the predicted DNA fragment. After that, the cell fluid analyte is discharged through the liquid outlet 34 of the DNA detection device 30. The detection process is simple and convenient on the premise of ensuring accurate detection.

Even though information and advantages of the present embodiments have been set forth in the foregoing description, together with details of the structures and functions of the present embodiments, the disclosure is illustrative only. Changes may be made in detail, especially in matters of shape, size, and arrangement of parts within the principles of the present embodiments to the full extent indicated by the plain meaning of the terms in which the appended claims are expressed.

What is claimed is:

1. A detection device, comprising:
a hollow pipe defining two openings; and
at least one sensor in the hollow pipe, each of the at least one sensor comprising:
an ultrasonic element, the ultrasonic element comprising:
a first electrode;
a second electrode facing and spaced apart from the first electrode;
an insulating layer on a side of the second electrode adjacent to the first electrode;
a vibrating film between the insulating layer and the first electrode, the vibrating film carrying the first electrode, wherein a cavity is formed between the vibrating film and the insulating layer; and
a receptor on a side of the first electrode away from the second electrode, wherein the receptor is configured to be combined with a target substance in a test analyte;
wherein the vibrating film is configured to vibrate to produce ultrasonic waves when the first electrode and the second electrode are applied with different voltages, the detection device further comprises a suction ball coupled to the hollow pipe, wherein the suction ball seals one of the two openings.

2. The detection device of claim 1, wherein the target substance is a sulfide, a ketone, an alcohol, or an olefin; and the receptor comprises a polymerizable polymer.

3. The detection device of claim 1, wherein the suction ball is made of an elastic material.

4. A detection device, comprising:
a first layer;
a second layer facing and spaced apart from the first layer;
a channel between the first layer and the second layer; and
at least one sensor in the channel, each of the at least one sensor comprising:
an ultrasonic element, the ultrasonic element comprising:
a first electrode;
a second electrode facing and spaced apart from the first electrode;
an insulating layer on a side of the second electrode adjacent to the first electrode; and
a vibrating film between the insulating layer and the first electrode, the vibrating film carrying the first electrode, wherein a cavity is formed between the vibrating film and the insulating layer; and
a receptor on a side of the first electrode away from the second electrode, wherein the receptor is configured to be combined with a target substance in a test analyte;
wherein the vibrating film is configured to vibrate to produce ultrasonic waves when the first electrode and the second electrode are applied with different voltages, the detection device is divided into a filtering section and a detection section coupled to the filtering section; the filtering section defines a liquid inlet the detection section defines a liquid outlet and the channel is coupled to both the liquid inlet and the liquid outlet; the at least one sensor is in the detection section.

5. The detection device of claim 4, wherein the first layer comprises a first hydrophobic layer, a first capping layer, and an electrode layer between the first hydrophobic layer and the first capping layer; the first hydrophobic layer is adjacent to the channel.

6. The detection device of claim 5, wherein the second layer comprises a second hydrophobic layer, a second capping layer, and a thin film transistor array layer between the second hydrophobic layer and the second capping layer; the second hydrophobic layer is adjacent to the channel.

7. The detection device of claim 6, wherein the thin film transistor array layer comprises a plurality of thin film transistors; each of the plurality of thin film transistors comprises a source electrode; a wetting performance of the test analyte is adjusted by adjusting voltages applied to the electrode layer and the source electrode.

8. The detection device of claim 6, wherein the detection device is configured to detect DNA.

* * * * *